United States Patent
VandeWoude et al.

(10) Patent No.: US 11,821,899 B2
(45) Date of Patent: Nov. 21, 2023

(54) **ENZYME-LINKED IMMUNOASSAY TO DETECT *FELIS CATUS* GAMMAHERPESVIRUS 1**

(71) Applicants: Susan VandeWoude, Fort Collins, CO (US); Kathryn R. Stutzman-Rodriguez, Springfield, IL (US); Ryan M. Troyer, London (CA)

(72) Inventors: Susan VandeWoude, Fort Collins, CO (US); Kathryn R. Stutzman-Rodriguez, Springfield, IL (US); Ryan M. Troyer, London (CA)

(73) Assignee: Colorado State University Research Foundation, Fort Collins, CO (US)

( * ) Notice: Subject to any disclaimer, the term of this patent is extended or adjusted under 35 U.S.C. 154(b) by 940 days.

(21) Appl. No.: 16/040,045

(22) Filed: Jul. 19, 2018

(65) Prior Publication Data

US 2019/0025306 A1    Jan. 24, 2019

Related U.S. Application Data

(63) Continuation of application No. 15/637,689, filed on Jun. 29, 2017, now abandoned.

(60) Provisional application No. 62/356,079, filed on Jun. 29, 2016.

(51) Int. Cl.
| | | |
|---|---|---|
| *G01N 33/53* | (2006.01) | |
| *G01N 33/569* | (2006.01) | |
| *G01N 33/49* | (2006.01) | |
| *G01N 33/535* | (2006.01) | |
| *C07K 14/03* | (2006.01) | |
| *G01N 33/68* | (2006.01) | |
| *C07K 14/005* | (2006.01) | |

(52) U.S. Cl.
CPC ..... *G01N 33/56994* (2013.01); *C07K 14/005* (2013.01); *C07K 14/03* (2013.01); *G01N 33/49* (2013.01); *G01N 33/535* (2013.01); *G01N 33/6854* (2013.01); *C12N 2710/16022* (2013.01); *G01N 2333/03* (2013.01); *G01N 2469/20* (2013.01)

(58) Field of Classification Search
CPC ........ G01N 33/56994; G01N 33/6854; G01N 33/49; G01N 33/535; G01N 2469/20; G01N 2333/03; C07K 14/005; C07K 14/03; C12N 2710/16022
See application file for complete search history.

(56) References Cited

U.S. PATENT DOCUMENTS 6,596,476 B1 *  7/2003  Lesniewski ........ G01N 33/5767
                                                                    435/5

OTHER PUBLICATIONS

Stutzman-Rodriguez et. al. (New Horizons in Translational Medicine , May 2015,vol. 2, issues 4-5, p. 131).*
Lerner et al., Nature 1982; 299:592-596.*
Labo et al and Supplement (PLOS 2014, vol. 10 issue 3 e1004046.*
Reisch et Reisch et al. Journal of Virological methods 1996;57, pp. 71-85.*
Millman et al. (Veterinary Microbiology, 2011;150, p. 15-20).*
Stutzman-Rodriguez et. al. poster date May 1, 2015 confirmed by USPTO library (New Horizons in Translational Medicine , May 1, 2015, vol. 2, issues 4-5, p. 131).*
Bennett et al. (2022, PLoS Pathogens 18(12):e1011033).*
Troyer et al. (Genome Announc Nov. 5, 2025; 3(6):e01192-15.*
Genebank FcaGHV1 (genome sequence was deposited in GenBank under accession No. KT595939 accessed on Jan. 16, 2023).*
Beatty et al. Felis catus gammaherpesvirus 1; a widely endemic potential pathogen of domestic cats. Virology. 2014. vol. 460-461: 100-107.
Piriou et al., Altered EBV viral load setpoint after HIV seroconversion is in accordance with lack of predictive value of EBV load for the occurrence of AIDS-related non-Hodgkin lymphoma. The journal of immunology. 2004. vol. 172: 6931-6937.
Troyer et al., Novel Gammaherpesviruses in North American Domestic Cats, Bobcats, and Pumas: Identification, Prevalence, and Risk Factors. Journal of Virology. 2014. vol. 88 (No. 8): 3914-3924.
Labo et al., Heterogeneity and breadth of host antibody response to KSHV infection demonstrated by systematic analysis of the KSHV proteome. PLoS Pathogens. 2014. vol. 10 (Issue 3): e1004046.
Katano et al., Identification of antigenic proteins encoded by human herpesvirus 8 and seroprevalence in the general population and among patients with and without Kaposi's sarcoma. Journal of Virology. 2000. vol. 74 (No. 8): 3478-3485.
Mbisa et al., Detection of antibodies to Kaposi's Sarcoma-Associated Herpesvirus: a new approach using K8.1 ELISA an a newly developed recombinant LANA ELISA. J Immunol Methods. 2010. vol. 356 (No. 1-2): 39-46.
Morrison et al., Serodiagnosis for Tumor Viruses. Semin Oncol. 2015. vol. 42 (No. 2): 191-206.
Stutzman-Rodriguez et al., Domestic cats seropositive for Felis catus gammaherpesvirus 1 are often qPCR negative. Virology. 2016. vol. 498: 23-30.
McLuckie et al., Molecular Diagnosis of Felis catus Gammaherpesvirus 1 (FcaGHV1) Infection in Cats of Known Retrovirus Status with and without Lymphoma. Viruses. 2018. vol. 10 (No. 128): 1-14.
Bartley et al., Identification of immuno-reactive capsid proteins of malignant catarrhal fever viruses. Veterinary microbiology. 2014. vol. 173: 17-26.
Klutts et al., Evidence-based approach for interpretation of Epstein-Barr virus serological patterns. Journal of clinical microbiology. 2009. vol. 47 (No. 10): 3204-3210.

(Continued)

*Primary Examiner* — Carmencita M Belei
(74) *Attorney, Agent, or Firm* — Michael M. McGaw; McGaw Law, P.C.

(57) ABSTRACT

Indirect ELISAs to detect exposure to *Felis catus* gammaherpesvirus 1 (FcaGHV1) in domestic cats. These ELISAs detect feline serum antibodies to ORF52 and ORF38 of FcaGHV1. The ELISA assays are sensitive, specific, and adaptable for scale up use in high throughput diagnostics.

7 Claims, 4 Drawing Sheets

Specification includes a Sequence Listing.

(56) References Cited

OTHER PUBLICATIONS

Lang et al., Comparison of the immunoglobulin-G-specific seroreactivity of different recombinant antigens of the human herpesvirus 8. Virology. 1999. vol. 260: 47-54.

Quinlivan et al., Longitudinal sero-reactivity to human herpesvirus 8 (KSHV) in the Swiss HIV Cohort 4.7 years before KS. J Med Virol. 2001. vol. 64: 157-166.

Zheng et al., Comparison of Humoral Immune Responses to Epstein-Barr Virus and Kaposi's Sarcoma-Associated Herpesvirus Using a Viral Proteome Microarray. Journal of Infectious Diseases. 2011. vol. 204: 1683-1691.

Detection of Immunodominant Proteins of Fells catus Gammaherpesvirus 1—Infona https://www.infona.pl/resource/bwmeta1.element.elsevier-e891b43c-e20a-30b9-895f-2f001a4faf6b/tab/summary as accessed on Jun. 28, 2021 at 8:05 AM.

GenBank: ALE14750.1—sequence for ORF38 [Fells catus gammaherpesvirus 1]—Protein—NCBI—as accessed on Jul. 6, 2021.

NCBI Reference Sequence: YP_001129391.1—sequence for ORF38 [Human gammaherpesvirus 8]—Protein—NCBI as accessed on Jun. 27, 2021.

GenBank: ALE14766.1—sequence for ORF52 [Fells catus gammaherpesvirus 1]—Protein—NCBI—as accessed on Jul. 6, 2021.

GenBank: QFU18761.1—sequence for ORF52 [Human gammaherpesvirus 8]—Protein—NCBI—as accessed on Jul. 9, 2021.

Mountain Scholar record for the thesis entitled "Seroanalysis of Fells catus gammaherpesvirus 1 infection in domestic cats" as accessed at https://mountainscholar.org/handle/10217/167233?show=full on Jul. 10, 2021 at 12 PM MST.

Stutzman-Rodriguez et. al., Detection of Immunodominant Proteins of Felis catus Gammaherpesvirus 1, New Horizons in Translational Medicine, vol. 2, Issues 4-5, May-Jul. 2015, p. 131.

Hou H, Wang T, Zhang B, Luo Y, Mao L, Wang F, Wu S, Sun Z. Detection of IgM and IgG antibodies in patients with coronavirus disease 2019. Clin Transl Immunology. May 6, 2020;9(5):e01136. doi: 10.1002/cti2.1136. PMID: 32382418; PMCID: PMC7202656.

* cited by examiner

ENZYME-LINKED IMMUNOASSAY TO DETECT *FELIS CATUS* GAMMAHERPESVIRUS 1

CROSS-REFERENCE TO RELATED APPLICATIONS

This application is a continuation of U.S. application Ser. No. 15/637,689, filed Jun. 29, 2017, which claims the benefit of U.S. Provisional Application No. 62/356,079, filed Jun. 29, 2016.

STATEMENT OF GOVERNMENT INTEREST

This invention was made with Government support under Grant No. T32 OD012201 awarded by National Institutes of Health. The Government has certain rights in the invention.

REFERENCE TO AN ELECTRONIC SEQUENCE LISTING

The contents of the electronic sequence listing (Patent-In Sequences-2076-38-PRC-13SEP2017_ST25.txt, Size: 3,915 bytes; and Date of Creation: Sep. 13, 2017) is herein incorporated by reference in its entirety.

FIELD OF INVENTION

This invention relates to screening for virus exposure in veterinary animals. More specifically, this invention relates to serologic testing to detect exposure to *Felis catus* gammaherpesvirus 1 (FcaGHV1) in domestic cats and other felines.

BACKGROUND OF THE INVENTION

The herpesviruses have 3 subfamilies: alpha, beta, and gamma. Alphaherpes viruses have more notoriety, causing mild to moderate disease and with potential to cause severe disease in the face of immunosuppresion. Many alphaherpesviruses also establish latency in sensory ganglia. The beta and gammaherpes viruses are lesser characterized; however they can still be powerful agents of disease. The gammaherpesviruses are known for being highly host specific and are often target B or T lymphocytes. Latent gammaherpesvirus is commonly found in lymphoid tissue.

Epstein-Barr virus (EBV) and Kaposi's sarcoma associated herpes virus (KSHV) are examples of human gammaherpesviruses. EBV causes mononucleosis upon initial infection and retreats into latency. Reactivation is associated with immunosuppression such as HIV infection. At this stage, EBV is associated with a range of lymphoproliferative disorders. Not as much is known about KSHV pathogenesis. KSHV causes mild disease, if at all, during primary infection instead it seems to require a cofactor to develop disease. Immune suppression appears to play a role as cofactor; under these circumstances KSHV causes Kaposi sarcoma, primary effusion lymphoma, multicentric Castleman's disease, and other non-Hodgkin lymphomas.

Prior to the discovery of *Felis catus* gammaherpesvirus 1 (FcaGHV1), there were no described gammaherpesviruses of the domestic cat. There is an available real time PCR (qPCR) assay that quantitates FcaGHV-1 viral DNA in whole blood samples. This assay aided identification of risk factors for FcaGHV1 infection. However, many questions remained unanswered about virus transmission, and disease association that could be addressed by development of serodiagnostics to detect viral exposure and test associations with disease states.

Studies of antigens for EBV and KSHV have revealed a variety of antigens with a varied response. In one KSHV study to evaluate seroprevalance of patients with KS, they did initial testing with a smaller set of KS patients on western blot for a variety of KSHV antigens. The goal was to discover which might be best used in an ELISA. This turned out to be a successful method for creating a sensitive ELISA, however they did note a fairly varied serologic response to the ELISAs they created for 5 antigens.

SUMMARY OF THE INVENTION

A high-throughput, sensitive, and specific serologic assay has been developed that is capable of detecting antibodies to FcaGHV1. During latency, intact herpes viral genomes are maintained in certain host cells, even though the virus is not actively replicating. Thus in general qPCR detection of gammaherpes (for example, EBV) is used to quantitate viral load and document viral activation. EBV reactivation and negative qPCR assay indicates latency or no infection. In contrast, a FcaGHV1 antibody detection assay will show a higher disease prevalence in the cat population than qPCR assay, because it will be able to detect cats infected with latent FcaGHV1 as well as cats with actively replicating virus. Secondarily, qPCR positive cats should also be seropositive, indicating that animals are mounting an active humoral immune response to FcaGHV1, infection.

*Felis catus* gammaherpesvirus 1 (FcaGHV1) is a recently identified agent that infects the domestic cat. Preliminary data indicates 16% prevalence among shelter cats in the United States. This data was based on a qPCR assay developed by the VandeWoude laboratory that identifies viral DNA in whole blood samples [Troyer, Ryan M., et al. "Novel Gammaherpesviruses in North American Domestic Cats, Bobcats, and Pumas: Identification, Prevalence, and Risk Factors." *Journal of virology* 88.8 (2014): 3914-3924]. FcaGHV1 was also detected in domestic cats in Singapore and Australia indicating endemism in distant geographic regions [Beatty, Julia A., et al. "*Felis catus* gammaherpesvirus 1; a widely endemic potential pathogen of domestic cats." *Virology* 460 (2014): 100-107]. Risk factors associated with FcaGHV1 include increased age, being male, co-infection with feline leukemia virus and feline immunodeficiency virus (FIV).

There are two human gammaherpes viruses, Epstein-Barr virus (EBV) and Kaposi's sarcoma-associated herpesvirus (KSHV). Infections with these viruses cause serious difficulties in the HIV patient. Patients co-infected with HIV and EBV have increased virus loads of EBV associated with EBV reactivation [Piriou, Erwan R., et al. "Altered EBV viral load setpoint after HIV seroconversion is in accordance with lack of predictive value of EBV load for the occurrence of AIDS-related non-Hodgkin lymphoma." *The journal of immunology* 172.11 (2004): 6931-6937]. We documented the same pattern of higher peripheral blood viral DNA loads in cats with both FIV and FcaGHV1 [Beatty, Julia A., et al, "*Felis catus* gammaherpesvirus 1; a widely endemic potential pathogen of domestic cats." *Virology* 460 (2014): 100-107]. EBV and KSHV have been difficult to model in vivo and there is a continual need to improve existing models and discover new ones [Chatterjee, Bithi, Carol Sze Leung, and Christian Münz. "Animal models of Epstein Barr virus infection." *Journal of immunological methods* 410 (2014): 80-87; Ganem, Don. "KSHV infection and the pathogenesis of Kaposi's sarcoma." *Annu. Rev. Pathol. Mech. Dis.* 1 (2006): 273-296.]. Further investigation into FcaGHV1 is needed to evaluate its potential as a model of human disease.

Our laboratory's qPCR measures viral load in the periphery. Based on related herpesviruses, this assay is likely only able to measure cats with actively replicating virus. Thus, latent FcaGHV1 infection is likely undetected with qPCR. We have thus been developing serologic methods to detect exposure to the virus. These two indirect enzyme-linked immunosorbent assays (ELISAs) we have developed detect antibody formation to FcaGHV1, providing a better measure of exposure to the virus and a sensitive of latent infection.

We developed indirect ELISAs using the gene products of ORF52 and ORF38. These gene products show homology to immunodominant antigens of other gammaherpes viruses, ORF38 of KSHV [Labo, N. et al. Heterogeneity and breadth of host antibody response to KSHV infection demonstrated by systematic analysis of the KSHV proteome. *PLoS pathogens* 10, e1004046 (2014)] and BLRF2(ORF52) of EBV [Reischl, Udo, et al. "Expression and purification of an. Epstein-Barr virus encoded 23-kDa protein and characterization of its immunological properties." *Journal of virological methods* 57.1 (1996): 71-85]. We initially transiently transfected the Crandell Rees Feline kidney cell line (CRFK) with an expression vector containing a gene inserts ORF52 and ORF38. Serum from 9 cats with high viral loads measure on FcaGHV1qPCR was tested with ORF52 and ORF38 IFA. ORF52 IFA showed 4 of these 9 cats positive and 7 of 9 cats were positive on ORF38 IFA. We developed a western blot assay for confirmation and re-tested serum from the same 9 cats. For ORF52, of the 4 cats that were positive on IFA, 2 were positive on western; the remaining 7 cats were negative. For ORF38 western blot the same 7 cats were positive. We then developed two ELISAs using ORF52 and ORF38 as the detection antigen. In the ORF52 ELISA, 8 of the 9 FcaGHV1 positive cats have a positive antibody response to ORF52. The ORF38 ELISA showed identical results to ORF38 IFA and western blot; the same 7 of 9 cats were consistently positive on all 3 assays.

We tested a group of 133 shelter cats with both ORF38 and ORF52 ELISAs. These cats had been previously tested with the FcaGHV1 qPCR assay [Troyer, Ryan M., et al. "Novel Gammaherpesviruses in North American Domestic Cats, Bobcats, and Pumas: Identification, Prevalence, and Risk Factors." *Journal of virology* 88.8 (2014): 3914-3924; Beatty, Julia A., et al. "*Felis catus* gammaherpesvirus 1; a widely endemic potential pathogen of domestic cats." *Virology* 460 (2014): 100-107] with a prevalence of 20/133 (15%). Of these 20 cats, 19 were positive on either or both ORF52 and ORF38 ELISAs, Prevalence calculated from the raw data for each assay was as follows: 30/133 (22.6%) for ORF38 ELISA, 41/133 (30.8%) for ORF52 ELISA. When results of the two ELISAs are compiled it yields a raw data seroprevalence calculation of 43/133 (32.3%).

To calculate assay sensitivity and specificity, we performed Bayesian statistical analysis on ORF38 and ORF52 ELISA results. We used the assumption that FcaGHV1 qPCR had 100% specificity and unknown sensitivity to calculate informative priors for a two-stage model. This method of analysis was recently described for assessing sensitivity and specificity without adequate access to a gold standard assay [Liu, Jin, et al. "A two-stage Bayesian method for estimating accuracy and disease prevalence for two dependent dichotomous screening tests when the status of individuals who are negative on both tests is unverified." *BMC medical research methodology* 14.1 (2014): 110]. Sensitivity of ORF52 ELISA was 74.3% (95% CI: 61 to 92.6), specificity was 96.4% (95% CI: 90.7 to 99.8). ORF38 ELISA had a sensitivity of 57.9% (95% CI: 50.3 to 73.8) and specificity of 97.9% (95% CI: 93.5 to 99.9). Using this same Bayesian model, seroprevalence of FcaGHV1 was estimated at 30.6% (95% CI: 21.6 to 41.1).

We noted some additional statistical associations when comparing qPCR positive results to ELISA positive results. Adult male cats were more likely to be both FcaGHV1 ELISA and qPCR positive which supports territorial fighting as a plausible route of transmission. There were some additional interesting trends with FcaGHV1 and other co-infections. FcaGHV1 qPCR positivity was better associated with detection of FIV antibodies p=0.057) than was FcaGHV1 seropositivity (p=0.1242). It could be that FIV immune suppression provides for reactivation of a latent FcaGHV1 infection leading to viremia that was detectable on our qPCR assay. In this situation it would make sense that ELISA positive animals would not be associated with FIV antibodies because this group could include animals with latent FcaGHV1. These are patterns that would fit those we see with concurrent HIV/EBV infection [Piriou, Erwan R., et al. "Altered EBV viral load setpoint after HIV seroconversion is in accordance with lack of predictive value of EBV load for the occurrence of AIDS-related non-Hodgkin lymphoma," *The journal of immunology* 172.11 (2004): 6931-6937]. Additionally detection of a *Bartonella* spp. infection by PCR was more associated with FcaGHV1 qPCR positive results (p=0.0547) than FcaGVH1-positive ELISA results (p=0.4921). There is some evidence to show that *Bartonella* spp. infection may cause complications in immune suppressed cats [Breitschwerdt, Edward B., et al. "Bartonellosis: an emerging infectious disease of zoonotic importance to animals and human beings." *Journal of Veterinary Emergency and Critical Care* 20.1 (2010): 8-30]. *Bartonella* spp. when detected in feline blood with PCR has been associated with febrile disease, but is more likely a cofactor in febrility and not as the sole cause [Lappin, Michael R., et al. "Prevalence of *Bartonella* species antibodies and *Bartonella* species DNA in the blood of cats with and without fever." *Journal of Feline Medicine and Surgery* 11.2 (2009): 141-1418]. This association between *Bartonella* spp. and FcaGHV1 infections could be rooted in a state of immune suppression. Both of the associations with *Bartonella* spp. and FIV provide some initial hints that FcaGHV1 could have a pathogenic role similar to that of KSHV and EBV demanding further investigation.

These results demonstrate that a combined ORF38/ORF52 ELISA provides an effective FcaGHV1 screening assay with an estimated sensitivity of 74.3% and 97.9% specificity. This is an assay that could be used to test seroconversion in investigative studies of FcaGHV1. We noted variations in associations to co-infection between FcaGHV1 seropositivity and qPCR positivity. This evidence shows that FcaGHV1 may have a pathogenic role similar to KSHV or EBV. Thus, this ELISA should prove to be a useful clinical tool.

ORF52 and ORF38 proteins are produced in transiently transfected 293T cells with a 6×-HA-tagged vector. The proteins are purified using the Pierce Magnetic HA-tag IP/Co-IP Kit. Quantification of purified protein are assessed by BCA assay and purity assessed by SDS page with coumasie stain. Each well of a 96 well plate is coated either with 40 ng of purified protein ORE52 or 100 ng of purified ORF38 diluted in 100 uL of 50 mM carbonate buffer (pH 9.5). Plates are incubated at 4 C overnight with the coating antigen. We perform a 2-hour block with 300 uL/well 2% BSA in imidazole wash buffer at room temperature. Serum is diluted 1:50 in the ELISA diluent and added at 100 uL/well to incubate at room temperature 2 hours. The plate is washed 5 times with 0.2% tween-imidazole wash buffer. Goat anti-cat IgG peroxidase conjugate is used as the secondary antibody at a 1:5000 dilution, adding 100 uL of the dilution/well and incubating 1 hour at room temperature. This is followed by 5 more washes and 100 uL per well of the TMB substrate/Peroxidase solution mix. The plate is incubated with the detection agent for 10 min at room temperature and stopped with 50 uL/well 2.5N $H_2SO_4$. Absorbances are read at 450 nm. Positive threshold is evaluated on a plate by plate basis: the mean absorbance and standard deviation of the replicates of the 3 SPF naïve cats are calculated. Threshold is defined as mean plus 3 standard deviations, if this calculation yielded a number <0.2, then 0.2 was considered the threshold for that 96-well plate.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
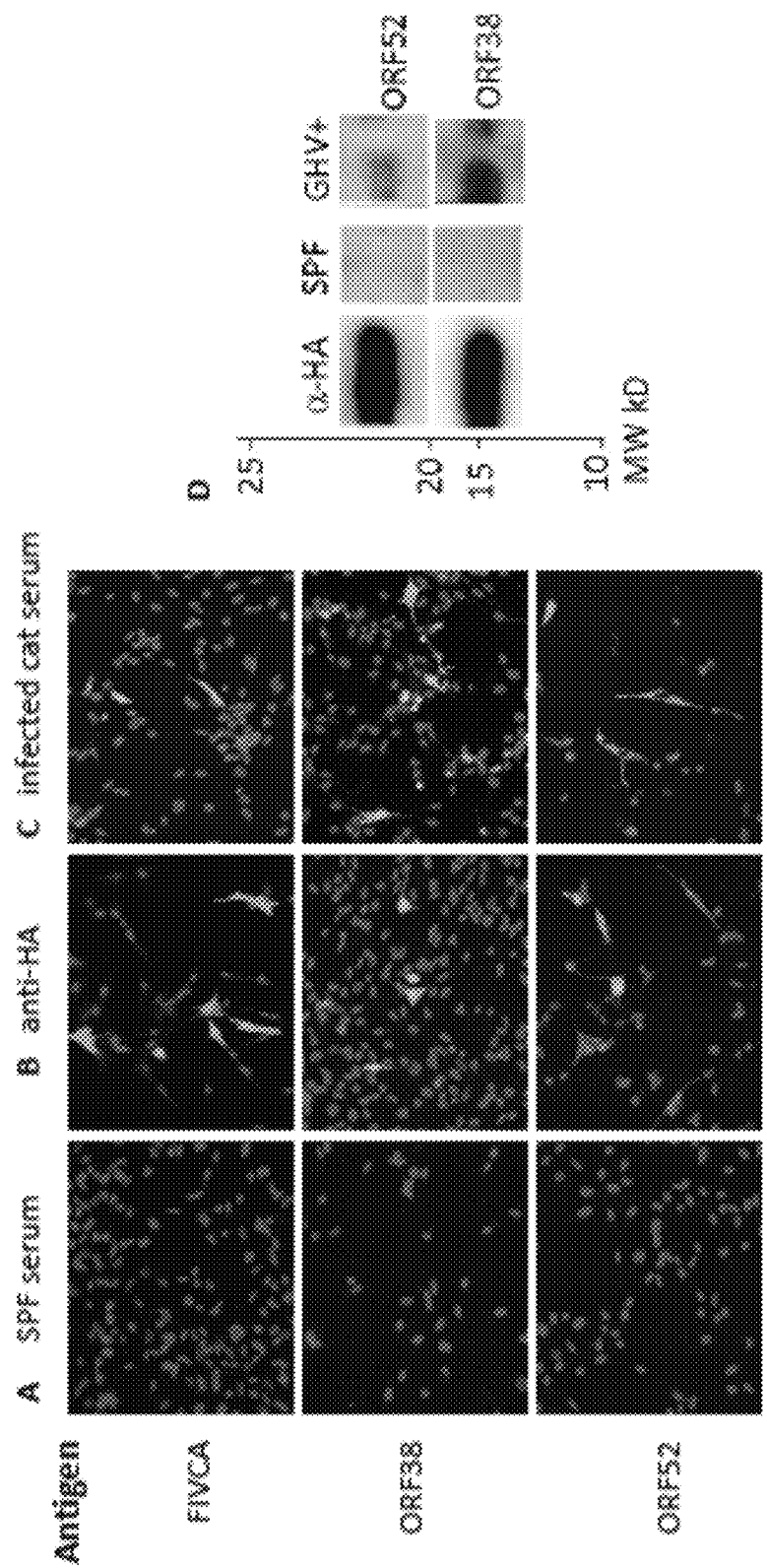
FIG. 1 is a series of images demonstrating that the immunofluorescence assay detects FcaGHV-1 antibodies in infected cats. The left-hand side of the figure indicates the recombinant protein antigen that was transfected into each set of cells. A. SPF cat serum was used as a negative control in all assays. B. Fluorescence indicates cells expressing the protein of interest with an HA tag. C. Serum from nine FcaGHV1-qPCR positive cats was used to screen each transfection reaction to determine if antibodies were present in cat sera for each antigen tested. Immunofluorescence indicates cells that bound cat serum antibody. Here we show results of one cat with proteins ORF38 and ORF52. The FIV capsid (FIVCA) was used as a positive control for detection of viral antigen when exposed to sera from FIV+ cats. A vector-only negative control was also run with each transfection (not shown). D. Western blot of ORF52 and ORF38 confirming IFA results. FIVCA=FIV capsid protein, ORF38=tegument protein of FcaGHV1, ORF52=tegument protein of FcaGHV1, anti-HA=antibody to HA.

*Felis catus* gammaherpesvirus 1 (FcaGHV1) was recently discovered in the domestic cat and potentially has a worldwide distribution. While only preliminary information has been established relating FcaGHV1 infection to demographic factors, other species of gammaherpes subfamily of Herpesviridae have been studied more in-depth. Most gammaherpesviruses (GHVs) are highly specific to their host species making it especially challenging to learn more about human GHVs. Epstein-Barr virus (EBV) and Kaposi's sarcoma-associated herpes virus (KSHV) are human GHVs that pose important health risks. Disease of EBV, KSHV and other GHVs appear to be more severe in immunocompromised individuals. For example, KSHV causes primary effusion lymphoma (PEL) in immune suppressed patients. PEL is a serious condition with median survival of 6 months even in patients undergoing currently accepted therapies. Further research on FcaGHV1 will not only benefit cat health, but could also provide a model of naturally occurring infection for better understanding of EBV and KSHV infection in humans.

All known herpes viruses establish a latent life-long infection. GHVs often cause lymphoproliferative disease as well as non-lymphoid cancers with re-activation from latency. For example, EBV often manifests as infectious mononucleosis upon initial infection, then persists in memory B-cells as a latent infection for the life of the individual. When the immune system is suppressed by old age, transplant surgery, and other infections, EBV can re-activate. EBV is strongly associated with Hodgkin lymphoma, non-Hodgkin lymphoma, Burkitt lymphoma, B-cell lymphoma of immunosuppression, and nasopharyngeal carcinoma. In contrast to EBV, initial infection of KSHV often does not cause disease. However, it is considered a necessary factor in the direct cause of several diseases: Kaposi's sarcoma, PEL, and multicentric Castleman disease in immune suppressed patients.

Herpes virion structure is similar across the family. Virion diameter ranges from 120-300 nm. It consists of a DNA core, followed by a capsid layer, tegument layer and envelope. The core of the herpesvirus is usually torus-shaped. The capsid has 162 capsomers including both pentameric and hexameric. Tegument is an ordered structure between the capsid and envelope. Layer thickness may vary across the virion and from one particle to another. Herpes viral envelopes are trilaminar with numerous short glycoprotein protrusions.

The relationship of feline immunodeficiency virus (Fly) and FcaGHV1 may provide a parallel opportunity to study HIV and human GHVs. FIV is already an established model for HIV because of the disease similarities. Patients co-infected with AIDS and either KSHV or EBV are at a greater risk of developing disorders related to these gammaherpes viruses. Treatment for GHV-related lymphoproliferative disease provides many challenges for the AIDS patient. There is a striking similarity between viral loads in EBV/HIV co-infection and FcaGHV1/FIV co-infection; cats that are co-infected with FIV and FcaGHV1 have higher viral loads of FcaGHV1. This pattern closely resembles HIV and EBV co-infection. Human viruses of the gammaherpesvirus subfamily are difficult to study because of the wide range of proteins that are expressed during lytic and latent phases of viral infection. Small animal model limitations have compounded this problem. There is a clear deficit of EBV animal models and a call for more work in this area. KSHV in vivo models are arguably even less robust. Investigators have gained a large body of information, which provides much of the current knowledge base on EBV from studying murine herpes virus 68 (MHV-68). One of the major obstacles to progress in the field using this model is that the virus biology for MHV-68 is in some ways more similar to the alphaherpesviruses rather than its own gammaherpesvirus subfamily. The humanized mouse model is promising, but it remains to be seen whether this model can truly address virus pathology. Using FcaGHV1 in cats to model this relationship could provide a unique, cost-effective opportunity to explore the relationship between HIV and EBV. However, additional diagnostics are needed to explore this potential model of disease.

Our lab developed a real time PCR (qPCR) assay that detected FcaGHV1 in 16% of US shelter cats and domestic cats infected with FcaGHV1 across three continents. Results of our qPCR assay revealed several risk factors for FcaGHV1, including being male, adult and evidence of co-pathogens. This suggests aggressive male encounters as a potential factor for FcaGHV1 transmission. Older age and a veterinary evaluation of "poor health" were also associated with FcaGHV1. The relationship to FcaGHV1 infection and co-infection status potentially implicates reactivation of FcaGHV1 due to immune suppression.

We hypothesized that the measure of prevalence from our qPCR assay is an underestimate of exposure to FcaGHV1 and latent infection. qPCR measures peripheral FcaGHV1 DNA viral load which is a measure of active viral replication and in gammaherpesviruses can be a good marker of primary infection or re-activation. An ELISA can assess humoral antibody status, which can indicate exposure but not necessarily an active infection. Due to similarities within the GHV subfamily, it is likely that FcaGHV1 viral-load variation in cats mimic those of EBV infection. If so, asymptomatic cats infected with FcaGHV1 would be seropositive but would have low or undetectable viral loads. The serologic assays developed in this project helped to resolve this question of exposure rate.

Here, we created an indirect ELISA to answer the question of feline exposure to FcaGHV1. Serum from 133 shelter cats that had previously been tested for FcaGHV-1 by blood cell qPCR was evaluated. We compared the data on age, sex, and co-infection status to evaluate differences between qPCR results and seroprevalence. Results identified seroprevalence as a measure of FcaGHV1 exposure and qPCR as a measure for active FcaGHV1 infection. This information provides a valuable contribution to the growing knowledge of FcaGHV1 and further information about its potential as a model of human GHVs.

EXAMPLE 1

Materials and Methods

Gene Selection for Identification of Immunodominant Antigens:

In a corollary study, our laboratory has obtained partial FcaGHV1 genome data to map FcaGHV-1 genes to other GHVs genes (unpublished data). We selected 7 conserved genes from this dataset to evaluate for potential to elicit humoral immunity in naturally infected cats. These included ORF38, ORF42, ORF59, ORF26, ORF52, ORF17.5, and ORF65 which code for proteins analogous to antigenic proteins of KSHV, EBV, and OvHV-2. All 7 proteins are virion-associated (Table 1).

TABLE 1

FcaGHV1 protein analogs are antigenic in other gammaherpesviruses.

| Gene | Type of protein | Analog to protein from | Possible function |
|---|---|---|---|
| ORF17.5 | Scaffold protein | MCFVs | Involved in capsid assembly |
| ORF38 | Tegument | KSHV | Support virion maturation in the cytoplasm |
| ORF52 | Tegument | EBV (BLRF2) | Assist virion egress and secondary envelopment |
| ORF65 | Capsid | EBV (BFRF3), KSHV, MCFVs | Small capsid protein, late gene |
| ORF26 | Capsid | EBV (BDLF1) | Capsid protein, late gene |
| ORF59 | Phosphoprotein | KSHV | Binds DNA polymerase and dsDNA to promote DNA synthesis by acting as a sliding clamp |
| ORF42 | Tegument | EBV (BBRF2) | May contribute to the regulation of mitochondrial function |

MCFVs include Ovine herpes virus 2 and Alcelaphine herpes virus 1. EBV has distinct gene nomenclature listed in parentheses.

Plasmids:

Specific primers with built in restriction sites were designed for each gene of interest based on our FcaGHV1 genome map (Table 2). All genes were PCR-amplified using a High Fidelity Platinum Taq PCR protocol from template DNA extracted from a cat infected with FcaGHV1 of confirmed sequence. PCR products were run on a 1% agarose gel to confirm expected nucleotide length. Bands were cut out and DNA extracted using the standard protocol from the Qiagen gel extraction kit. Concentration of amplicon DNA was evaluated with a NanoDrop spectrophotometer.

Reactions for restriction digest of amplicons were setup exactly as outlined by the New England Biolab NEBcloner online protocol development tool for digests in 50 uL reactions. BamHI HF and EcoRI HF were used to cut all gene amplicons and the pKH3 vector except ORF17.5, BclI was used in place of BamHI for ORF17.5 restriction digest and the coordinating vector digest. After digest, the reactions were run on a 1% agarose gel and bands of the expected nucleotide length were extracted and purified with the Qiagen gel extraction kit. The NanoDrop spectrophotometer was again used to evaluate concentration.

These restriction enzyme digested amplicons were then ligated into the pKH3 vector using corresponding cloning sites and New England Biolab T4 DNA ligase and coordinating manufacturer protocol for cohesive ends. Reactions were each 20 uL and ligation performed using a molar ratio of 1:3, vector to insert. The pKH3 vector which contains an HA tag, was a gift from Joel Rovnak and Sandra Quackenbush.

Plasmid constructs were transformed in OneShot Chemically Competent cells using suggested protocols by the manufacturer. Ten colonies from each transformation were screened by PCR targeting each insert and products were run on a gel to ensure that the insert was the correct nucleotide length. Three colonies of appropriate insert size were selected to propagate overnight in Lysogeny broth (LB)+ampicillin. Inserts from selected colonies were sequenced to confirm identity and 1 clone with insert of perfect sequence was selected. A glycerol stock was created for the selected colony for long term storage. Plasmid was purified from this selected colony using the Qiagen plasmid mini and midi spin prep protocols.

The FIV capsid protein, used as a control for the immunofluorescence assay, was acquired from a previous study. It had been cloned into a pGEX2T vector with the same reading frame pkH3. Restriction digest was performed with the FIVCA-pGEX2T using BamHI HF and EcoRI HF with the same protocols as described earlier for the other constructs. The product was run on a 1% agarose gel to select the correct insert size and purified using the Qiagen gel purification kit. All the following steps described earlier were performed identically to the other constructs, that is: ligation of FIVCA into pkH3, transformation, storage, and plasmid purification.

were tested with serum from all nine FcaGHV1-positive cats. Transfected cells were also tested with negative control serum from three specific pathogen-free (SPF) cats from the CSU SPF retrovirus research cat colony. This colony has been extensively screened and shown to be FcaGHV-1 negative. An FIV-antigen capsid protein was used to transfect CRFK cells as described above; exposure to banked FIV-positive serum was used to demonstrate successful transfection and appropriate IFA parameters. Additionally, to test for protein expression by evaluating the presence of the

TABLE 2

Primers used to amplify FcaGHV1 genes and pKH3 vector.

| Gene | Primers |
| --- | --- |
| ORF17.5 | 5'-AGACGCTGATCAATGGCCACTAATGCCAG-3' [SEQ ID No. 1]<br>5'-CCTGAATTCCTATTAGTTTTTTAGAAGTTCTTCACAAAATA-3' [SEQ ID No. 2] |
| ORF38 | 5'-CGCGGATCCATGGGTATCATCTGCTCTATTT-3' [SEQ ID No. 3]<br>5'-CCGGAATTCCTATCAGATACTAAATACAACTTTCTTTTTTATC-3' [SEQ ID No. 4] |
| ORF52 | 5'-CGCGGATCCATGGCTTCTAAAAAAGGAACACC-3' [SEQ ID No. 5]<br>5'-CCTGAATTCCTATTAGGTTGGTTGTTTGGATCTAC-3' [SEQ ID No. 6] |
| ORF65 | 5'-CGCGGATCCATGAGTAGGGAACAGTTAAGAG-3' [SEQ ID No. 7]<br>5'-CCGGAATTCCTATTATTTTTTTTTGCTTCCACTAGTTG-3' [SEQ ID No. 8] |
| ORF26 | 5'-CGCGGATCCATGCAAGTTGATAAAAAAATCATAGTC-3' [SEQ ID No. 9]<br>5'-CCGGAATTCCTACTAGATGGACAACCAGCCT-3' [SEQ ID No. 10] |
| ORF59 | 5'-CGCGGATCCATGGAAGCTAAAATTACTACTCACTA-3' [SEQ ID No. 11]<br>5'-CCGGAATTCCTATTATGTTGTAATCTTGGAATGTTTTG-3' [SEQ ID No. 12] |
| ORF42 | 5'-CGCGGATCCATGGACTCTGTAATCCGAACC-3' [SEQ ID No. 13]<br>5'-CCTGAATTCCTATTATGAAAAGATTTGTACTCTAGGCTT-3' [SEQ ID No. 14] |
| pKH3 | 5'-CAACTGCACCTCGGTTCTA-3' [SEQ ID No. 15]<br>5'-CCATTATAAGCTGCAATAAACAAGT-3' [SEQ ID No. 16] |

Immunofluorescence Assay:

CRFK cell cultures were maintained with CRFK media made from low glucose DMEM+glutamax (Life Technologies brand), with added 10% fetal bovine serum (FBS), 1% sodium bicarbonate, 1% Penicillin/Streptomycin (Pen-strep) and 1% non-essential amino acids. For additional culture maintenance, they were passaged when confluent (bi-weekly) using trypsin.

For the immunofluorescence assay (IFA), CRFKs were grown on glass slides with twelve 0.4 mm wells with the CRFK media mentioned earlier except for no added antibiotic. CRFKs were plated at 5,000 cells per well and incubated for 2 days to allow adherence to the slide. Slides were individually contained within separate petri dishes with sterile water to maintain humidity. Transfections with plasmid constructs were performed using Lipofectamine 2000 protocols in 0.4 mm well, using 0.15 uL Lipofectamine and 60 ng plasmid per well. Cells were incubated for 21 hours. This time length was selected as optimal for transfection efficiency of FIVCA, this time was kept the same for all transfections and no further experiments were done to optimize time length to specific genes used in the transfection.

After incubation, slides were gently washed with PBS to remove excess media. Cells were then fixed using 2% paraformaldehyde and 50:50 ethanol/methanol followed by air-drying. The experimental serum used was obtained from nine cats sampled at shelters in CO, CA, or FL previously shown to have high peripheral FcaGHV1 DNA viral loads. Each set of cells transfected to produce the selected proteins HA tag included in each vector, cells were incubated with Covance rabbit-anti-HA at a 1:500 dilution. Slides were incubated for 1 hr at 37 C with primary antibodies followed by three more washes with PBS in preparation for secondary antibody exposure.

The secondary antibody used for the rabbit-anti-HA was Covance anti-rabbit FITC diluted to 1:500. Secondary antibody to detect feline serum antibodies (Covance anti-cat-IgG FITC) was used at 1:50 and incubated 1 hr at 37 C followed by 3 PBS washes and a 2 min DAPI stain. All sera mentioned earlier and commercial antibody was diluted in 2% bovine serum albumin (BSA) in PBS. All sera were diluted at 1:20 in BSA/PBS and commercial antibodies at the listed ratios in BSA/PBS. Slide covers were sealed with ProLong Gold Antifade prior to light microscopic viewing (with an Olympus BX60) for immunofluorescence.

Positive results were recorded if there was at least one cell per well that had a stronger immunofluorescence than the strongest background visible on the (negative) wells exposed to SPF naïve serum. This immunofluorescence was also compared to surrounding negative cells within the well when evaluating positive versus negative. Images were recorded with the microscope-connected Olympus DD71 digital capture system. Uniform adjustments were made with Photoshop to improve overall brightness of images for presentation.

Western Blot for Confirmation of Immunodominant Antigens:

Immunoblot analysis was performed to confirm IFA observations on two candidate antigens demonstrating the most consistent immunofluorescence against qPCR positive FcaGHV-1 cat sera. ORF38 and ORF52 were purified from cell lysates (transfection conditions using Lipofectamine 2000 described earlier scaled-up for 6-well tissue culture plates) using the Pierce magnetic anti-HA IP/co-IP kit and following manufacturer instructions. Protein quantification was determined using the Pierce BCA kit NuPage 1.5 mm, 4-12% Bis-Tris 10 well gels were used in the NuPage gel box with associated 20× Nupage MES Running Buffer (1M Tris-Base, 1M MES, 2.0%SDS, 2niM EDTA) diluted to 1× working buffer. The power supply was set at 160V for 40 min. For each protein being evaluated, 1ug of protein per well was used, with enough wells to evaluate the different samples. The Bio-Rad Precision Plus Blue and Magic Mark standards were run for each gel.

Gels were transferred to PVDF membrane using 1× working stock of the 20× NuPage transfer buffer with added 10% methanol. The gel and PVDF membrane were sandwiched between 9 layers of blotting paper. Transfers were done in a Trans-Blot Turbo Transfer System at 15V for 30 min. The PVDF membrane was blocked for 1 hour with 5% milk protein in PBS, and then cut into strips for exposure to serum from 9 qPCR positive cats and 3 SPF naïve cats at 1:20 dilution in PBS for 1 hour. The strips were then washed in PBS plus 2% tween (PBST). The strips were incubated with goat anti-cat phosphatase labeled IgG for 1 hour at 1:2000 in PBS. After an additional wash, strips were incubated with BCIP-NBT phosphatase substrate to visualize bands.

To ensure the correct protein was on the membrane, one strip with each protein was incubated with Covance HA.11 mouse anti-HA antibody at 1:5000 and secondary goat anti-mouse HRP at 1:10000. Dilutions were in PBS and washes were performed as described earlier with serum incubated strips. Equal amounts of peroxidase and luminol were applied to the strip and then visualized using chemiluminescent detection imaging (ImageQuant LAS 4000).

Protein Expression for ELISAs:

ORF 38 and ORF52 were chosen for larger-scale production in 293T cells. 293T cells were maintained in 293T media (high glucose DMEM with added 2% Glutamax, 10% FBS, and 1% Pen/Strep). Cells were maintained by passaging when confluent on a biweekly basis.

Eight million 293T cells were plated onto 100 mm tissue culture plates in antibiotic free media and incubated overnight at 37 C. Plasmid constructs that were developed for the IFA were transfected the following day with 45 uL Lipofectamine 2000 and 18 ug plasmid per plate for ORF52 and 60 uL Lipofectamine 2000 and 15 ug plasmid for ORF38. Optimem was used in the quantities recommended by Lipofectamine 2000 manufacturer protocols. Transfection length was found to be optimal at 20 hours. Cells were harvested and purified using the Pierce anti-HA magnetic bead kit and protein concentration determined by BCA assay, as described earlier, and stored at 4 C.

ELISAs:

ELISAs were performed in 96-well plates. Each protein was diluted in a 50 mM carbonate buffer, 40 ng ORF52 in 100 uL buffer per well and 100 ng ORF38 in 100 uL buffer per well. Plates were incubated overnight at 4 C. Contents were discarded and 300 uL of 2% BSA in imidazole-buffered saline (IBS) was used to block plates for 2 hours at room temperature. Contents of block were discarded and wells were incubated at room temperature for 2-hours with 100 uL serum per well, diluted 1:100 in ELISA diluent made with IBS. Plates were washed 5 times in a plate washer with IBS+0.2% Tween (IBST).

The secondary incubation was 1-hour at room temperature with 5% mouse sera ELISA diluent and 1:5000 Cappel goat anti-cat IgG peroxidase conjugate. Wells were again washed in plate washer 5 times IBST. TMB-peroxidase detection solution was added to each well (100 uL) and incubated for 10 min at room temperature. The reaction was stopped using 50 uL per well of 2.5N $H_2SO_4$. Absorbencies were read at 450 nm. Serum from each cat was run in triplicates and controls run in triplicate on each plate included serum from 3 SPF naïve cats, no-antigen control wells, and diluent-only wells.

Prior to initiation of sample testing each ELISA was tested with serum from 10 SPF naïve cats to ensure that there was no non-specific reaction occurring. Positive threshold was evaluated on a plate-by-plate basis: the mean absorbance and standard deviation of the replicates of the 3 SPF naïve cats was calculated. Positive threshold was defined at mean plus 3 standard deviations, if this calculation yielded a number <0.2, then 0.2 was considered the threshold for that 96-well plate.

Collection of Samples:

Domestic cat blood samples were obtained from archived samples of ostensibly healthy animals. These samples were taken from cats upon admission to shelters Florida, California, and Colorado as previously described. [Troyer, R. M. et al. Novel Gammaherpesviruses in North American Domestic Cats, Bobcats, and Pumas: Identification, Prevalence, and Risk Factors. *Journal of virology* 88, 3914-3924 (2014)] FcaGHV1 qPCR assay prevalence was performed on DNA extracted from blood cells as previously described. Demographic data were recorded for each cat, also described previously. Each cat was also previously evaluated for Calicivirus, Feline herpesvirus-1 (FHV1), *Mycoplasma* spp., *Bartonella* spp. and FIV. Calicivirus and FHV1 were evaluated by oral swab PCR. *Bartonella* spp. was tested both by IgG and PCR. *Mycoplasma* spp. and FIV were both tested by presence of antibody.

Statistical Analysis:

Logistic regression was used to make statistical analysis of geographic data and FcaGHV1 qPCR or ELISA result. Shelter and state were each modeled as categorical independent-variables along with sex and age as binary co-variables. In each model, FcaGHV1 ELISA result or qPCR result was the dependent (response) variable. Binary logistic regression was used to model each co-infection. FcaGHV1 ELISA or qPCR result was the binary dependent-variable and the co-infection, sex, and age as independent binary co-variables. For sex and age, male was recorded as 1 and female as 0, similarly adult as 1 and young as 0. Odds ratios were calculated within the respective logistic models. Linear regression was used to evaluate correlation of absorbance and qPCR viral load. Logistic and linear regression modeling were performed in SAS.

Sensitivity and specificity was calculated using modeling techniques described by Liu et al. [Liu, Jin, et al. "A two-stage Bayesian method for estimating accuracy and disease prevalence for two dependent dichotomous screening tests when the status of individuals who are negative on both tests is unverified." *BMC medical research methodology* 14.1 (2014): 110.] This Bayesian model requires a gold standard test used to evaluate only the positive responses from two dependent screening tests along with positive and negative results from those assays. This was adapted to our study by considering the two ELISAs (ORF38 and ORF52) to be the dependent assays. The qPCR assay was considered a gold standard only for the sake of specificity (100%). As with the model designed by Liu et al, two sensitivities were calculated for the ELISAs based on the association to qPCR specificity, only cats testing positive on qPCR were considered in this evaluation. This information was then used as informative priors for a second model to calculate specificity and sensitivity for each ELISA assay as well as prevalence. We used the open access WinBugs program written by Liu et al to make these calculations.

EXAMPLE 2

Results

Expression Plasmid Development and Controls:

FcaGHV1 genes were selected from the FcaGHV1 genome (unpublished data) based on genome alignment to determine homologous genes that code for antigens of KSHV, EBV and malignant catarrhal fever causing viruses (MCFVs) (Table 1—presented above). The pKH3 vector used for all plasmid constructs contains an HA tag that was expressed along with the protein of interest. The HA tag was used as a control measure to evaluate protein expression in CRFK cells with both IFA and western blot (See FIGS. 1B&D). As a positive control, CRFK cells were transfected with the antigenic, FIV-capsid protein (FIVCA) and exposed antigen to FIV-positive serum in both the IFA (FIG. 1) and western blot (data not shown). FIVCA was inserted in the same pKH3 vector and treated under the same conditions as other proteins. Transfection conditions for both IFA and western blot were optimized to FIVCA protein.

IFA:

To determine which proteins of FcaGHV1 elicited IgG antibody during a natural infection, we developed an immunofluorescence assay to screen and evaluate seven FcaGHV1 proteins. Cells were fixed with paraformaldehyde and methanol/acetone. This exposed the transfected intracellular proteins to subsequently added antibodies. All CRFKs were also stained with DAPI. We were able to visualize immunofluorescent cells for all protein transfections after exposure to anti-HA antibodies with a FITC tag (See FIG. 1B). All cells exposed to cat sera were subsequently incubated with an anti-cat-IgG FITC to visualize immunofluorescence. We confirmed assay controls: FIVCA transfections exposed to FIV-positive serum antibodies (FIG. 1A-C) and negative control SPF cat serum (FIG. 1A). We screened each of the seven FcaGHV1 antigens following transfection (Table 4) with serum from nine FcaGHV1-positive cats with high peripheral-DNA viral loads. We assumed these animals should have detectable antibodies against FcaGHV-1 antigens. ORF38, ORF65, ORF17.5, and ORF52 all had measurable serum antibody reactivity against one or more of the FcaGHV1-positive cat sera (Table 4, FIG. 1). ORF38 and ORF52 antigens reacted against more individual FcaGHV-1 positive cat samples (Table 3, Table 4). No immunofluorescent antibody response was detected against ORF26, ORF59, or ORF42.

TABLE 3

Variation was evident across types of ORF52 antigen assays but not ORF38 assays.

| PCR + | ORF38 | | | ORF52 | | |
|---|---|---|---|---|---|---|
| cat# | IFA | wb | ELISA | IFA | wb | ELISA |
| G1 (CA) | + | + | + | + | − | + |
| G2 (CO) | − | − | − | + | − | + |
| G3 (CA) | + | + | + | + | − | + |
| G4 (CA) | + | + | + | − | − | + |
| G5 (FL) | − | − | − | − | − | − |
| G6 (FL) | + | + | + | − | − | + |
| G7 (CA) | + | + | + | − | − | + |
| G8 (FL) | + | + | + | − | − | + |
| G9 (FL) | + | + | + | + | + | + |
| Total pos. | 7 | 7 | 7 | 4 | 1 | 8 |

TABLE 4

IFA and western blot results for remaining proteins tested

| | ORF59 | ORF65 | | ORF17.5 | ORF26 | ORF42 |
|---|---|---|---|---|---|---|
| | IFA | IFA | wb | IFA | IFA | IFA |
| G1 | − | − | + | − | − | − |
| G2 | − | − | − | − | − | − |
| G3 | − | + | + | + | − | − |
| G4 | − | − | − | − | − | − |
| G5 | − | − | − | − | − | − |
| G6 | − | − | − | − | − | − |
| G7 | − | − | − | − | − | − |
| G8 | − | − | − | − | − | − |
| G9 | − | + | − | − | − | − |
| total pos. | 0 | 2 | 2 | 1 | 0 | 0 |

Nine cat samples positive for FcaGHV1 on qPCR were used for antigen identification screening. Table shows which cats displayed a serum antibody response to ORF52 and ORF38 proteins on each respective immunofluorescence assay (IFA), western blot (wb), and ELISA.

Western Blot Analysis:

We confirmed IFA results for ORF52, ORF38, and ORF65 via western blot by immobilizing partially purified viral antigens versus sera from the same 9 FcaGHV1 positive individuals (FIG. 1D, Table 3, Table 4). Serum from 3 SPF cats was run against all proteins and was consistently negative (FIG. 1D). Western blots were performed with crude lysate for all proteins, but background was too high to make conclusions except for FIVCA reactivity with FIV+ serum (data not shown).

Indirect ELISA Optimization:

Given indications of reactivity against ORF38 and ORF 52, we proceeded to develop two indirect ELISAs with these antigens. We scaled-up production of protein in 293T cells using similar techniques employed for CRFK transfection in IFA and western blot. ORF52 had a consistently higher protein yield after purification: 0.5 ug/million cells transfected. Despite transfection optimization experiments ORF38 only produced 0.2 ug protein/million cells transfected.

Both ORF38 ELISA and ORF52 ELISA were screened with 10 SPF naïve cats revealing all negative results. Additionally every 96-well plate included 3 SPF naïve cats to define threshold calculations (data not shown). We tested serum from 9 cats evaluated on IFA and western blot (Table 3) during assay development. Once assays were optimized, we repeated with these cats and additional animals representing shelter animals across the US, for a total of 133 cats.

Figure 2:
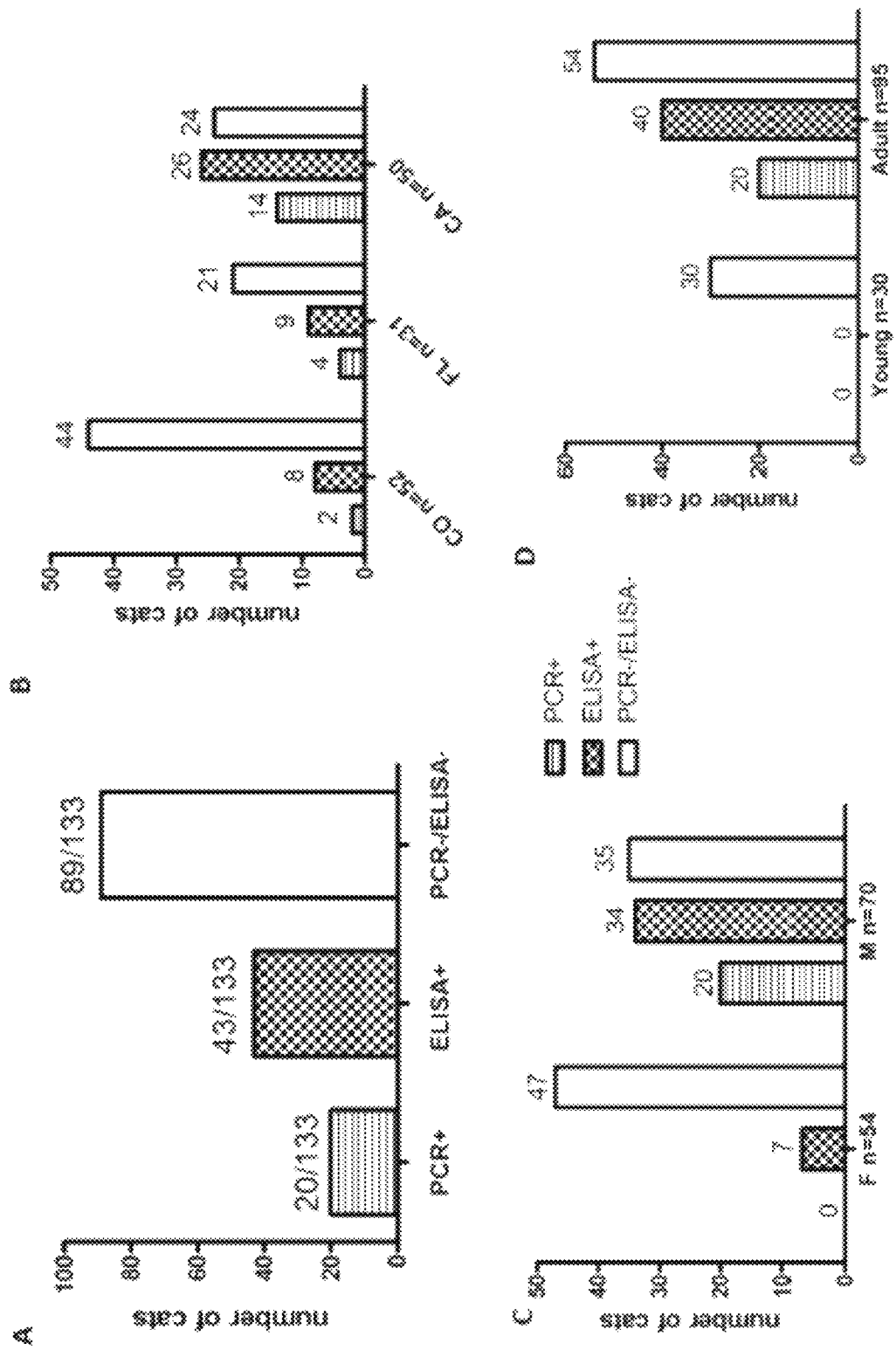
FIG. 2 is a set of four histograms showing the uniform increase in seroprevalance compared to qPCR prevalence that was evident across location, sex, and age categories. A. Comparison of FcaGHV1 serology to qPCR (previous publication) prevalence data for all shelter cats tested across the USA, n=133. One adult male cat from Florida was PCR+/ELISA−. All other PCR+ animals were also ELISA+. B. Comparison of assay results by location: Colorado, Florida, and California. C. Assay comparison by sex: male (M) and female (F). Unknown sex not shown: n=9, D. Assay comparison by age. Unknown age not shown: n=8.

Comparison of Seroprevalance and qPCR Results:

To compare viral loads and immune responses, we surveyed 133 cats previously tested for FcaGHV-1 prevalence via qPCR assay of peripheral whole blood FcaGHV1 DNA. These cats represented animals presented to 8 different shelters in three different states in a period of 2-3 years depending on the shelter. The original cohort contained 135 cats; however we did not have serum samples archived for 2 cats, so they were removed from the sample set. We detected 15% (20/133) qPCR positivity (16% was published previously with the full 135 animal sample set) and 32% (43/133) overall seropositivity after combining results of the two antigens for the ELISAs (FIG. 2A). Of the 20 cats that tested positive on qPCR, 19 also tested positive on serologic assay making up 44% of FcaGHV1 seropositive animals. Thus, there were 22 cats testing negative on qPCR and positive on the combined serologic assay (Table 5 and FIG. 2A).

it was considered ELISA positive for comparison of regional data, risk factors, and co-infection status. We compared assay results by qPCR and ELISA with demographic information including location of the shelter cat, sex and age (FIG. 2B-D). We noted a uniform increase from qPCR prevalence to ELISA prevalence by location, sex, and age categories reflective of the overall increase in prevalence with the ELISA assay (FIG. 2A-D). Seroprevalence increased when compared to qPCR, prevalence in Colorado from 4% to 15%, Florida from 13% to 29%, and California from 28% qPCR prevalence to 52% seroprevalence. Prevalence on qPCR was 0% for females while seroprevalance was 13%. Male cats increased from a 29% qPCR prevalence to 49% seroprevalence. Young cat qPCR prevalence and seroprevalance remained at 0% in stark contrast to 21% qPCR prevalence in adults with a 42% seroprevalence (FIG. 2B-D).

TABLE 5

FcaGHV1 ELISA results coincide with qPCR and show additional positive results.

| A | ORF52 ELISA+ | ORF52 ELISA− | B | ORF38 ELISA+ | ORF38 ELISA− | C | ORF52 ELISA+ | ORF52 ELISA− |
|---|---|---|---|---|---|---|---|---|
| ORF38 ELISA+ | 28 | 2 | qPCR+ | 17 | 3 | qPCR+ | 18 | 2 |
| ORF38 ELISA− | 13 | 90 | qPCR− | 13 | 100 | qPCR− | 23 | 90 |

Categorical data comparison of cats tested for all 3 assays: ORF38 ELISA, ORF52 ELISA, and evidence of qPCR FcaGHV1 viral DNA load.

Table 5 displays the categorical data results of each assay in comparison to the qPCR results from our previous publication. ELISA results generally supported each other; only 1 cat was positive only by qPCR (ELISA negative), 1 cat was positive only with the ORF38 ELISA (ORF52 and qPCR negative) and 11 cats were only positive by ORF52 ELISA (ORF38 and qPCR negative). All other cats were confirmed by at least 2 assays. To further support specificity of ELISAs, there was a positive trend with qPCR measured viral load vs ELISA absorbances for both ORF38 and ORF52. ANOVA analysis of the linear regression model showed no significance indicating little variation from 95% confidence limits.

Sensitivity and Specificity:

A two stage Bayesian method was used to evaluate sensitivity and specificity of the ORF38 ELISA and the ORF52 ELISA. Sensitivity of ORF52 ELISA was 74.3% (95% CI: 61 to 92.6), specificity was 96.4% (95% CI: 90.7 to 99.8). ORF38 ELISA had a sensitivity of 57.9% (95% CI: 50.3 to 73.8) and specificity of 97.9% (95% CI: 93.5 to 99.9). Using this same Bayesian model accounting for sensitivity and specificity of the ELISAs, seroprevalence of FcaGHV1 was estimated at 30.6% (95% CI: 21.6 to 41.1).

FcaGHV1 Predictors and Risk Factor Analysis:

For the rest of the analysis we combined the ELISA results so that if a cat was positive with one or more antigens We used logistic regression to find associations with the ELISA results for risk factors previously evaluated by qPCR (Table 6). The risk factor of adult vs young (p=0.011), male vs female (p=0.0001), were corroborated from previous risk factors identified with qPCR testing. Adult male cats are more likely to participate in territorial fights, which may affect transmission. Additionally, adults have a longer amount of time to contract infection. These factors could explain the increased odds for adult and male cats to be seropositive. Male cats were 7.11 (CI: 2.623, 19.288) times more likely than females to be FcaGHV1 seropositive. The odds ratio for FcaGHV1 seropositivity in adult cats was 43.7 (CI: 2.379, 800.766). The odds for a male cat, compared to female, to be qPCR positive was 43.975 (2.581, 749.124) and adult vs young 9867 (CI: 1.951, mi). It should be noted that wide confidence intervals are a reflection of the statistical modeling limits. There were no young cats that were either seropositive or qPCR positive for FcaGHV1 and no female cats that were qPCR positive. The result of this is quasi-complete separation of the data set which was accounted for using Firth's penalized likelihood. This allows calculation of odds ratios and p values but with wide confidence intervals.

TABLE 6

Differences in significance of co-infection data when comparing FcaGHV1 ELISA to qPCR.

| | y = ELISA | | | | | y = qPCR | | | | |
|---|---|---|---|---|---|---|---|---|---|---|
| | OR | 95% CI | P (Wald) | n | pos. $x_n$ | OR | 95% CI | P (Wald) | n | pos. $x_n$ |
| Male | 7.11 | 2.623 to 19.288 | 0.0001 | 122 | 69 | 43.975 | 2.581 to 749.124 | 0.009 | 124 | 71 |
| Adult | 43.7 | 2.379 to 800.766 | 0.011 | 122 | 94 | 9.867 | 1.951 to ∞ | 0.004 | 124 | 96 |

TABLE 6-continued

Differences in significance of co-infection data when comparing FcaGHV1 ELISA to qPCR.

| | y = ELISA | | | | | y = qPCR | | | | |
|---|---|---|---|---|---|---|---|---|---|---|
| | OR | 95% CI | P (Wald) | n | pos. $x_n$ | OR | 95% CI | P (Wald) | n | pos. $x_n$ |
| Bart. IgG | 2.72 | 0.993 to 7.468 | 0.0516 | 117 | 30 | 3.148 | 1.051 to 9.425 | 0.0404 | 119 | 30 |
| Bart. PCR | 1.57 | 0.432 to 5.726 | 0.4921 | 117 | 17 | 3.988 | 0.973 to 16.352 | 0.0547 | 119 | 17 |
| FIV | 3.07 | 0.734 to 12.869 | 0.1242 | 120 | 15 | 3.983 | 0.959 to 16.532 | 0.057 | 121 | 15 |
| Mhm | 11.3 | 3.736 to 33.895 | <.0001 | 115 | 35 | 3.369 | 1.098 to 10.339 | 0.0338 | 117 | 36 |
| Mhf | 4.9 | 0.74 to 32.396 | 0.0995 | 115 | 11 | 2.271 | 0.536 to 9.620 | 0.2656 | 117 | 11 |
| Calicivirus | 1.07 | 0.279 to 4.121 | 0.9184 | 118 | 15 | 0.865 | 0.201 to 3.713 | 0.8453 | 120 | 15 |
| FHV1 | 9.61 | 0.484 to 190.741 | 0.1377 | 118 | 6 | 2.552 | 0.414 to 15.715 | 0.3124 | 120 | 6 |

Predictor variables and coinfection data for FcaGHV1 positive serology. P value from Wald testing shows significance of binary logistic regression modeling with FcaGHV1 ELISA result or qPCR result as the response variable (y). Separate models were created with each co-infection as independent variables (x) along with sex and age as co-independent variables. Odds (OR with 95% confidence interval) of a positive FcaGHV1 ELISA or qPCR result were calculated for each independent variable. This table also shows the number of animals in each model (n) and the number of positive animals for each independent variable within that sample (pos. $x_n$). In the case of male and adult, the positive $x_n$ column refers to number of male cats and number of adult cats.
Bart. = *Bartonella* spp.
Mhm = *Mycoplasma haemominutum*,
Mhf = *Mycoplasma haemofelis*,
FHV1 = Feline herpesvirus 1. Both FHV1 and Calicivirus were tested by oral swab PCR and FIV, Mhm, and Mhf were evaluated with PCR testing.

There was a significant difference in ELISA result between locations capture by state p=0.0176 (Table 7). Similar differences also exist in the qPCR data, p=0.052. The widest separation of odds was California vs Colorado for both a FcaGHV1 qPCR positive result and EL SA positive result. California locations had the highest density of feral cats among the three states. Cats from California were 4.65 (CI: 1.601, 13.503) times more likely to be ELISA positive and 4.916 (CI: 1.286, 18.786) times more likely to be qPCR positive than cats from Florida. There wasn't a significant difference in odds between California and Florida in either qPCR or ELISA FcaGHV1 result. There was no significant difference between shelter within the states with our qPCR analysis (p=0.402), we did see a significant difference between shelters in our ELISA results (p=0.0429). Odds ratios were calculated to compare shelters within states only. There were no significant differences between shelters in Colorado or Florida (data not shown). However in California, cats captured by Ventura Animal Services were 8.613 (CI: 1.257 to 59.018) times more likely to be seropositive when compared to cats captured by San Diego Feral Cat Coalition (Table 7). Although the locations of capture are within 250 miles of each other, cats from Ventura Animal Services were in areas of high human population density while the cats from San Diego were captured in rural areas of the Peninsular mountain range.

We further evaluated associations of FcaGHV1 serology with a co-infection. Samples from these animals have previously been tested for 6 other infections: FIV, *Bartonella* spp., *Mycoplasma haemominutum* (Mhm), *Mycoplasma haemofelis* (Mhf), Calicivirus, and Feline herpesvirus 1 (FHV-1). Odds ratios and p values are summarized in Table 7. *Bartonella* spp. IgG was similarly associated to both FcaGHV1 ELISA and qPCR positivity. There was a near significant association with positive *Bartonella* spp. IgG response and FcaGHV1 seropositive response (p=0.0516) and a significant association with FcaGHV1 qPCR positive cats (p=0.0404). In contrast, *Bartonella* spp PCR response differed between the two FcaGHV1 test groups. There was a clear absence of significance with a *Bartonella* spp. PCR positive result and FcaGHV1 seropositivity (p=0.4921) while qPCR positivity and positive *Bartonella* spp. PCR had a near significant association (p=0.0547). There was a similar dynamic as with *Bartonella*. spp. PCR to associations with FIV antibody response. Positive result of FcaGHV1 ELISA showed no association with FIV antibody positive results (p=0.1242), while FcaGHV1 qPCR and FIV association was nearly significant (p=0.057). *Mycoplasma haemominutum* (Mhm) and *Mycoplasma haemofelis* (Mhf) were also previously tested for by PCR. Mhm was significant for both FcaGHV1. qPCR positive (p=0.0338) and ELISA positive cats (p<0.0001). Mhf was not significant for

TABLE 7

Comparison of FcaGHV1 ELISA and qPCR results yields little variation in geographic data.

| | y = ELISA | | | y = qPCR | | |
|---|---|---|---|---|---|---|
| | P (Wald) | OR | 95% CI | P (Wald) | OR | 95% CI |
| State | 0.0176 | — | — | 0.052 | — | — |
| California vs Colorado | — | 4.65 | 1.601 to 13.503 | — | 4.916 | 1.286 to 18.786 |
| California vs Florida | — | 1.567 | 0.449 to 5.467 | — | 0.941 | 0.217 to 4.078 |
| Florida vs Colorado | — | 2.967 | 0.788 to 11.171 | — | 5.223 | 0.942 to 28.964 |
| Shelter | 0.0429 | — | — | 0.402 | — | — |
| Ventura vs San Diego | — | 8.613 | 1.257 to 59.018 | — | 2.189 | 0.320 to 14.985 |
| Ventura vs Corona | — | 1.942 | 0.336 to 11.215 | — | 0.7 | 0.135 to 3.616 |

P values were calculated for differences by state or shelter using categorical logistic regression modeling with sex and age as co-independent variables and qPCR or ELISA result as the response variable (y). Odds ratios (OR) were calculated to compare shelters in California: Ventura Animal Shelter, San Diego Feral Cat Coalition, and Corona Animal Shelter. Odds ratios between Colorado and Florida shelters were not significant (not shown).

either FcaGHV1 assay result, but much closer to significance for FcaGHV1 ELISA (p=0.0995) than qPCR (p=0.2656). Calicivirus and FHV1 positive results were far from significance for both FcaGHV1 positive assay results.

As hypothesized, a higher prevalence of FcaGHV1 in a population of 133 shelter cats via ELISA (32%) compared to qPCR positive individuals (15%) was detected. Antibody response reflects exposure to the virus, while qPCR assay measures an active or reactivated viral infection. From this analysis we conclude that close to half (44%) of FcaGHV1 exposed cats have an active FcaGHV1 infection. Our measured FcaGHV-1 seroprevalence is much lower than the seroprevalence of EBV in humans. EBV has a global seroprevalence of greater than 95% indicating very promiscuous spread of this agent. The seroprevalence of FcaGHV1 in cats more closely resembles the seroprevalence of KSHV in humans. There is wide variation in KSHV seroprevalance rates partly because there is no gold standard assay; however, it never reaches levels as high as EBV. KSHV exposure ranges dramatically by region. North America, Asia, and Europe are considered low seroprevalence areas and most studies have indicated exposure rates of <5%. However, one study which tested routine pediatric patients in southern Texas by immunofluorescence assay, ELISA, and immunoblot found a seroprevalence of 26%. Higher KSHV seroprevalence, approximately 50%, is found in regions of Africa and also the Brazilian Amazon.

Studies to date have suggested FcaGHV1 has a closer phylogenetic relationship to KSHV than EBV, and it has genes homologous to KSHV that are not conserved in other gammaherpesviruses, such as LANA (unpublished data). Assuming that the FcaGHV-1 ELISA was sensitive enough to identify most of the cats exposed to FcaGHV1, seroprevalance is below 50% as with KSHV. KSHV's lower seroprevalence and high regional variation might be due to factors involved with virus shedding. With EBV, even latently infected healthy adults can continue to shed virus in oral secretions, 20-30% of healthy adults at any point in time. High rates of KSHV shedding in healthy adults is individual specific and highly sporadic. Variation in KSHV shedding plays a role in regions with high rates of mother-to-child transmission through direct contact with saliva. There is evidence to show that this KSHV persistent shedding is related to host genetic factors. Interestingly, no young cats (n=30) were seropositive for FcaGHV1, and there are very few female cats in this population that are seropositive (7/54) and none that were qPCR positive. This suggests that mother-to-kitten transmission is not the primary mode of FcaGHV1 transmission, and aggressive contacts are a more likely mode of spread. FcaGHV1 may also have similar host genetic factors to KSHV that cause some infected cats to be more or less likely to shed virus. An increase in KSHV replication is associated with development of KS. It is worth looking for a similar pattern with FcaGHV1 and feline neoplastic disorders.

The results of this ELISA data strongly corroborate age and sex as risk factors for FcaGHV1 that were identified previously. Being male and adult appears to be strongly associated both with active FcaGHV1 infection (qPCR data) and exposure (ELISA results). These may be patterns associated with route of transmission or there could be genetic factors associated with being male and viral replication. This new ELISA data also showed a potential correlation between exposure to FcaGHV1 and co-infection with other pathogens, which was also true for FcaGHV1 qPCR results. This might be related to pathogenesis of FcaGHV1 and also to routes of transmission.

With the assumption that reactivated FcaGHV1 infection should follow immune suppression, one might expect to see an association with multiple co-infections in cats FcaGHV1-positive on an assay that measures active infection (qPCR) and no association in cats positive an assay thought to measure FcaGHV1 exposure (ELISA). Instead, ELISA-positive cats showed an increased association with co-infections when compared to previously reported qPCR-positive results. Some of the co-infections looked at included *Bartonella* spp., *Mycoplasma* spp., and FIV measured by IgG. A lower IgG titer is merely in indication of a past infection for Which we made no separate distinction in this analysis. High IgG titers for multiple infections could be an indicator of immune suppression, but still is probably not the best way to measure immune competence. IgG can vary depending on the microbe and potential for re-infection events that might not directly reflect host immune status. What the results showed instead was an increase in prevalence observed with the FcaGHV1 ELISA that bolstered statistical power allowing for a significant association where we previously noted trending results. This is particularly true with FIV, since there were relatively few cats testing positive for FIV in our US sample set (11 out of 96). Additionally, it may be that an increased antibody response to ORF38 and ORF52 is associated with some variable of FIV infection in an FcaGHV1 infected cat. Studies of KSHV sero-reversion in longitudinal studies of HIV patients have demonstrated plasticity of KSHV antibody titers throughout HIV infection and relative to development of KS.

Our previous research supports intraspecific fighting as a route of transmission. [Beatty, J. A. et al. *Felis catus* gammaherpesvirus 1; a widely endemic potential pathogen of domestic cats. *Virology* 460-461, 100-107, doi:10. 1016/j.virol.2014.05.007 (2014).] Coincident co-infections observed in this study could reflect similarities in route and risk of transmission through fighting. *Bartonella* spp., *Mycoplasma*. spp., and FIV are all thought to be transmitted via antagonistic encounters. Additionally, adult male cats would be most likely to participate in territorial fights. Human gammaherpesviruses can be transmitted through direct contact with saliva. EBV is transmitted mostly through salivary secretions. The most current information suggests saliva as the major route for KSHV infection as well. Initially it was thought that KSHV was transmitted sexually. More recent studies have shown that KSHV viral secretions are highest in oral mucosa, with further evidence of high seroprevalence estimates from populations of children where vertical transmission probably plays a minor role.

Sensitivity and specificity are difficult to measure without a gold standard test. In order to use Bayesian probability, at least 2 tests must be compared. The two assay types in this study, qPCR and ELISA do not evaluate the same thing, active viral infection vs viral exposure. Therefore, sensitivity and specificity cannot be evaluated with this method. However, ORF38 and ORF52 ELISA assays could be evaluated using a Bayesian logistic regression model. The accuracy of estimates is only as good as the probability distributions of my known parameters. A better method which could be used with future development of more assays or more) would be to use latent class modeling, modified for sensitivity and specificity calculations.

Figure 3:
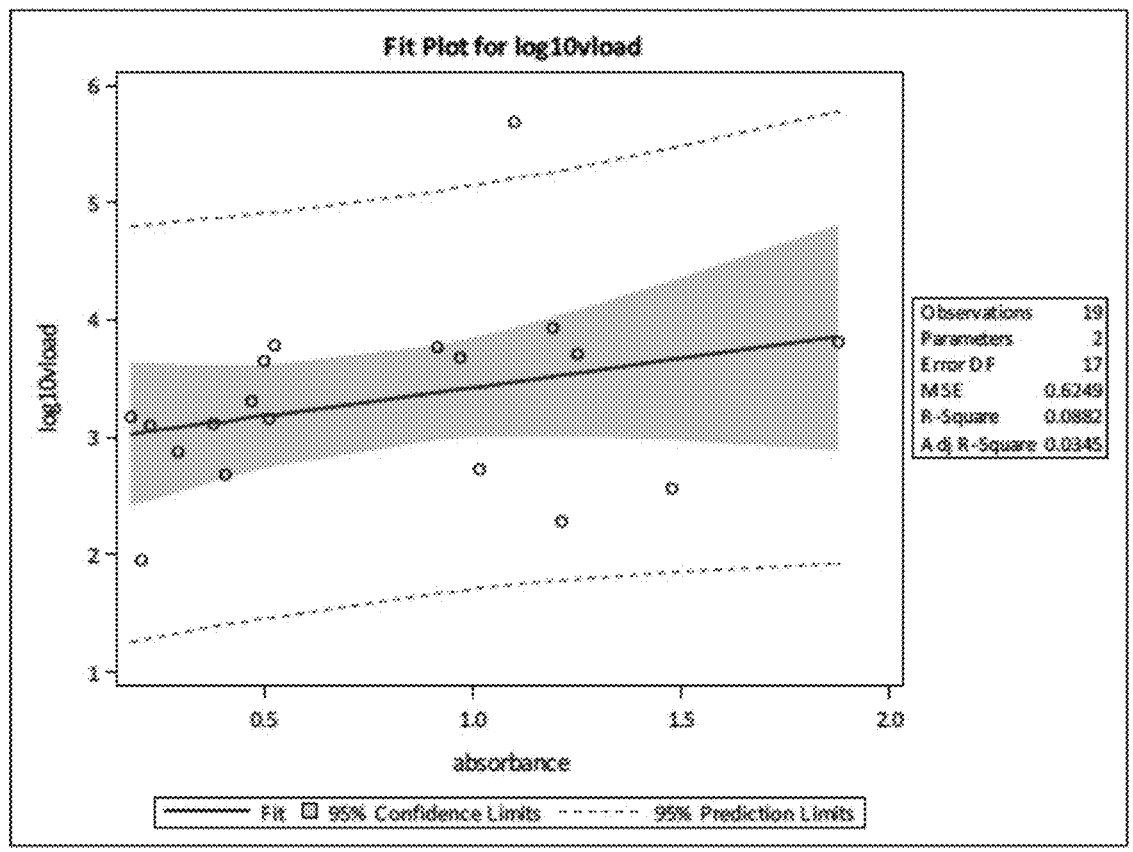
FIG. 3 is a graph showing the viral load vs. serologic assay absorbance for ORF52, which shows a positive trend.
Figure 4:
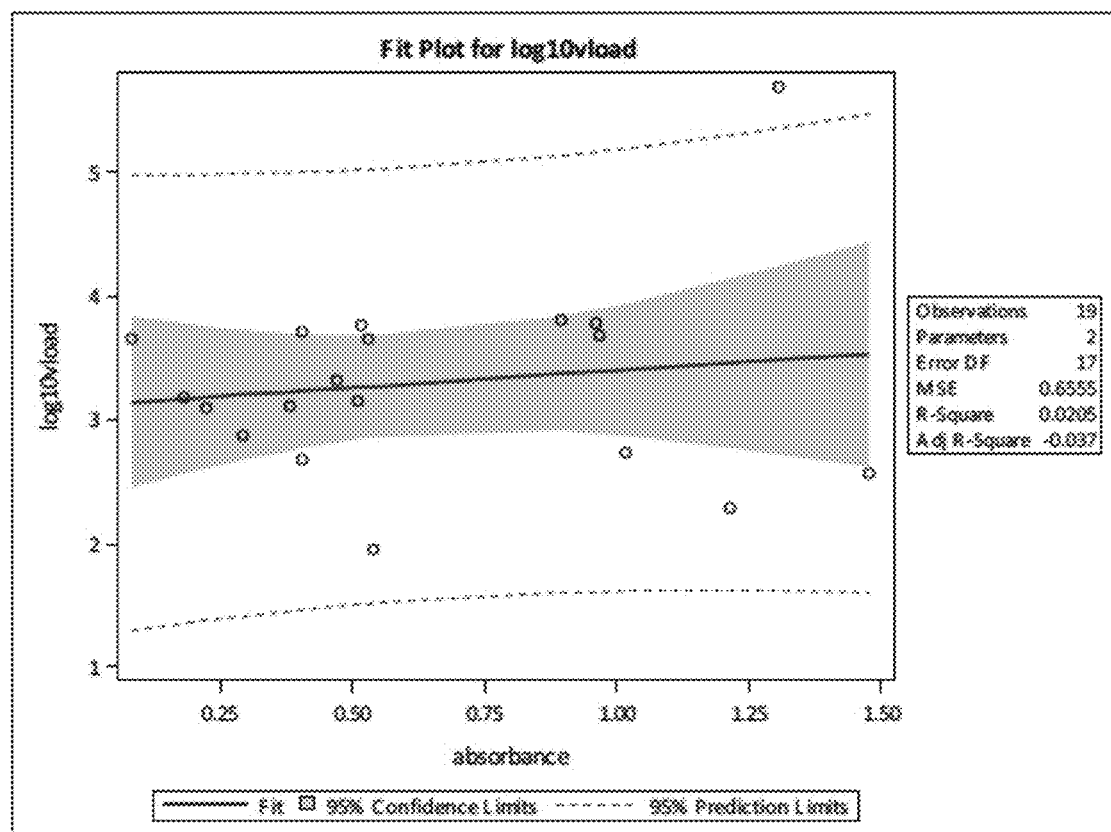
FIG. 4 is a graph showing the viral load vs serologic assay absorbance for ORF38, which also shows a positive trend.

There are additional reasons to have more confidence in specificity of this ELISA. The positive correlation between viral load and ELISA absorbance provides evidence of ELISA specificity (FIGS. 3 and 4). We also recorded that 19/20 qPCR positive cats were positive on ELISA. Both of these results provide more assurance that qPCR–/ELISA+ results are accurate. As noted, only one cat (G5 from Florida) was qPCR positive and negative on both ELISAs. Cat G5 had a relatively high whole-blood viral-DNA load recorded initially and during retesting (4491 copies/million cells). This animal was also negative on both ORF65 and ORF17.5 IFAs. Negative serology and positive qPCR could be explained by a recent infection that had not yet resulted in seroconversion. Other explanations include the individual's inability to produce antibodies due to severity of some other immune problems or a sample identification error.)

Most likely the correlative viral load vs ELISA absorbance (FIGS. 3 and 4) also reflects a situation where most of the cats that are qPCR positive in this sample set are cats with a re-activated infection or a late stage primary infection. In both of these situations antibody titer and viral load are high. Reactivation would result in higher levels of viral antigen in circulation, which would boost anamnestic humoral immune response, causing higher antibody loads.

An estimate of how many cats might have an active FcaGHV1 infection in a given year gives more information about potential for virus transmission. The samples used in this study were collected at each site over a 2 to 3 year period depending on exact site. The estimate using qPCR prevalence data would be about 5 to 8 cats out of a 100 cats annually with an active infection. This is not a true measure of incidence since a primary infection cannot be detected by ELISA or qPCR assay. Based on kinetics of EBV serology patterns, an individual who is in late primary infection would have a similar profile as someone with re-activated infection. Additionally, viral-DNA load in the blood could also be similar for both infection stages. It is therefore difficult to come to a conclusion about primary versus re-activated infection. However, the rate of 5-8 cats out of 100 annually with an active infection does give some idea about chances of transmission. Considering a cat fight might be required for transmission, this rate of infected animals would also be congruent with interpreting FcaGHV1 seroprevalence (35%) as a measure of exposure. Density is another important factor in considering transmission rate, since these cats were mostly free-range animals prior to shelter admission, one could further evaluate this through information about feral cat densities at each site.

The IFA and western blot testing proved to be an effective method of screening immunodominant antigens of FcaGHV1 to target certain proteins for high throughput antibody screening. The combination of these initial tests allowed confirmation that at least some domestic cats with FcaGHV1 would form antibodies to ORF38 and ORF52. Western blot proved to be a valuable technique in further characterizing immune responses indicated by IFA screening assays. The combination of these assays provided more confidence against false negatives on the ELISAs developed. In the future, they would be good complements to data on new antigen testing, but they could be performed after ELISA development as confirmation.

There were some potential background issues on both IFA and western blot. The alkaline phosphatase method of detection had a fairly high level of background that limited western blot diagnostic utility and may have contributed to the lack of sensitivity with ORF52. It was noted that there was a higher level of background on IFA when looking at samples exposed to cat serum as opposed to the anti-HA antibody. This included SPF naïve cat serum and the background was particularly intense around the nucleus of the CRFKs. This was likely a generalized reaction of feline serum to the particular feline cell line or to ubiquitous cell culture contaminants. Most of the proteins, including tegument proteins ORF38 and ORF52, appeared to localize to the cytoplasm or a combination of cytoplasm and nucleus of the CRFKs. However, ORF59 localized only to the nucleus. Background nuclear staining could have masked ORF59 positive results. ORF59's localization to the nucleus during transient transfection may be explained by the function of ORF59 gammaherpesvirus homologues as the DNA polymerase processivity factor. In KSHV, there is some evidence that ORF59 forms a homodimer when it enters the cytoplasm. If this were the case in FcaGHV1 as well, the dimerization may have concealed the HA tag on the recombinant construct making it only visible in the nucleus.

There was variation in individual cat antibody response with respect to each antigen of FcaGHV1 evaluated in this study. ORF38 and ORF52 proteins both reacted with 65% of all seropositive cats, 5% only reacted with ORF38 and 30% only with ORF52. Of the 15 cat sera samples that only reacted with one antigen, 20% were also confirmed by qPCR-positive results. Variation in humoral immune response is certainly not uncommon but it may be more pronounced during gammaherpesvirus infection. Katano et al evaluated seroprevalance in patients with KS for a variety of KSHV antigens. [Katano, H. et al Identification of antigenic proteins encoded by human herpesvirus 8 and seroprevalence in the general population and among patients with and without Kaposi's sarcoma. *Journal of virology* 74, 3478-3485 (2000).] They performed initial testing with a smaller set of KS patients using western blot, and noted that seroreactivity to antigens was not uniform. Because of the wide range in response, they created a more sensitive ELISA for 5 antigens. The results for cats tested in this assay reflect a similar varied antibody response. Variation may be a due to a combination of the complexity of gammaherpesvirus life cycle, variations in host immune response, and technicalities of assay development.

ORF38 and ORF52 did not have uniform performance across IFA, western blot and ELISA (Table 3). The ORF38 ELISA detected 2 individuals positive that were ORF52 ELISA negative while ORF52 detected 13 individuals that were ORF38 ELISA negative. There were 28 cats that were positive on both ELISAs (Table 4). This difference between IFA, western blot, and ELISA could be explained by some factor in the conditions of the IFA or the western blot that did not allow proper expression of ORF52. An alternative explanation may relate to optimization of the ELISA assay. ORF38 had a rather low yield of protein per transfection. Transfection efficiency was optimized by adjusting amounts of transfection reagents and harvesting at different time points for ORF38. However, despite this, at best production only yielded half of the protein production per million cells as with those exposed to ORF52 transfection. Since we have not yet synthesized and purified large quantities of protein for ELISA optimization, additional assay development may enhance the sensitivity of ORF38 as a serologic target. Enhancement of antigen production would be a logical next step for standardizing ORF38 and ORF52 ELISAs for large-scale reproducible use.

The antigens identified as immunodominant (ORF38 and ORF52) in this analysis represent tegument proteins in other gammaherpesviruses. The tegument is a layer of the virus between the envelope and the capsid. In general herpesvirus proteins have multiple highly distinct functions. ORF38 and ORF52 also potentially provide more efficient virion maturation and egress. These additional roles may mean high production of these proteins and contribute to other aspects of their antigenic nature. The proteins that form the tegument are particularly understudied in herpes viruses. Studies of Herpes Simplex Virus (HSV) have revealed that HSV particles are coated with tegument in the cytoplasm of the host cell. This corresponds to localization of these tegument proteins to the cytoplasm during transient transfection (FIG. 1). HSV tegument proteins are known to have roles beyond structure formation including activation of glycoproteins and capsid proteins. There is also evidence that tegument proteins have roles in binding to cellular transport proteins. These additional functions may increase exposure to the host immune system. Additionally, variation in pathogen recognitions factors likely plays an important role.

KSHV data suggests that sensitivity of mixed-antigen ELISAs can increase with use of a combination of latent and lytic protein antigens. In this study we did not evaluate proteins that are considered to be homologous to herpesvirus proteins expressed during latency. There is potential to pursue this in the future with the FcaGHV1 homologue to KSHV's latency-associated nuclear antigen (LANA). That said, the ELISAs developed in this study are likely a fairly accurate measure of exposure, it could be a small percentage that are being missed by not evaluating further antigens. A case-control study would be the ideal setting to evaluate a full panel of screening ELISAs tested sequentially during FcaGHV1 infection to advance understanding of the FcaGHV1 life cycle.

A case-control study of cats that have been coinfected with FIV and FcaGHV1 would allow for in-depth study of many aspects of FcaGHV1. Coinfected cats would be compared to uninfected cats as well as cats with a singular infection. This study has the potential to quickly answer questions discussed earlier about FcaGHV1 transmission, pathogenesis, and viral kinetics. It could provide information about actual clinical disease associations with FcaGHV1 and the value of developing therapeutics. Studying EBV and KSHV has been difficult because they are complex viruses with large DNA genomes. Furthermore, the associated lifelong latency periods make study of transmission and reactivation even more difficult. These aspects have also made vaccine development challenging. Good animal models allow us to better study these sorts of details rather than relying on human longitudinal studies that attempt to make up for an inability to manipulate study variables. Consequently, one of the most important benefits of feline case-control studies of FcaGHV1 would be to evaluate the potential for a feline model of HIV/GHV co-infection of humans.

The combined results of the tegument associated antigens ORF52 and ORF38 ELISA make for a good measure of FcaGHV1 exposure. As a complement to this assay, the FcaGHV1 we developed previously is a good measure for viral load. We concluded that a little less than half of seropositive cats likely have an active FcaGHV1 infection.

This study additionally showed strong support of risk factors of FcaGHV1 infection identified previously. Adult male cats are much more likely to be both seronegative and have peripheral-blood viral load. There was also a more robust relationship between co-infection and seropositivity. All of these things together point strongly toward cat fights as a mode of transmission.

It may appear from this data set that ORF52 ELISA is just as good as a stand-alone assay. However, given what we know about individual and regional variations in seroresponse of KSHV, it is believed the ORF38 ELISA is an important addition to the ELISA. Ideally, antigens could be optimized for use in a multiplex assay. Additions of other antigens to the ELISA could also be explored, preferably in settings of more controlled experimentation such as case-control studies.

IFA and western blot assays proved to be useful tools for bolstering assurance of specificity during ELISA development. In the future they will be helpful techniques that could also be used after ELISA development instead of before. To improve the ELISA assay a more productive method of producing ORF38 and ORF52 will also be important.

Other results of this study showed more similarities to KSHV than EBV. This might become useful in future efforts to model KSHV disease. It would be important to design studies aimed at identifying disease associations and routes of transmission. Ideally, the next step would be to select populations of cats where there is access to both whole blood and serum. One could then target disease patterns such as chronic lymphocytic leukemia, inflammatory bowel disease, B cell lymphocytosis, and intestinal lymphoma and assess both FcaGHV1 seropositivity and qPCR. Based on our knowledge of gammaherpesviruses and common clinical syndromes in cats that have lymphoproliferative tendencies, these would be the most likely diseases to have an association with FcaGHV1.

GLOSSARY OF CLAIM TERMS

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "Western blot assay" refers to an analytical technique used to detect specific proteins in a given sample of tissue homogenate or extract. It utilizes gel electrophoresis to separate either native proteins or denatured proteins by their lengths or 3-D structures. The separated proteins are transferred to a membrane (typically nitrocellulose or PVDF), and are detected using antibodies specific against a target protein.

As used herein, the term "antibody" refers to an immunoglobulin produced by B cells and has structural units of two large heavy chains and two small light chains. There are two general classes of antibody; namely, monoclonal antibody and polyclonal antibody. Monoclonal antibodies (mAb) refer to monospecific antibodies that are the same because they are made by identical immune cells that are all clones of a unique parent cell. Monoclonal antibodies are typically made by fusing myeloma cells with the spleen cells from a mouse that has been immunized with the desired antigen. Polyclonal antibodies are antibodies obtained from different B cells. They are a combination of immunoglobulins secreted against a specific antigen, each identifying a different epitope. Animals frequently used for polyclonal antibody production include goats, guinea pigs, rabbits, horses, sheep and the like. Rabbit is the most commonly used laboratory animal for this purpose.

As used herein, the term "protein" refers to a chain of at least two amino acids. The terms "polypeptide," "peptide," or "protein" are used interchangeably.

The term "ELISA" (also known as Enzyme-linked immunosorbent assay) refers to a biochemical technique used mainly to detect the presence of an antibody or an antigen in a biological sample.

The term "indirect ELISA" refers to a biochemical technique where an unknown amount of antigen is affixed (i.e., immobilized) to a solid surface, and then a antibody (that recognizes the antigen) is added onto the surface so as to allow the forming an antigen-antibody complex. The antigen-antibody complex is detected by a secondary antibody. Detection may be achieved by direct linking an enzyme to the secondary antibody or indirect via another antibody with an enzyme. The enzyme often converts to some detectable signal, most commonly a color change in a chemical substrate.

The term "sandwich ELISA" (also known as Capture ELISA) refers to immobilizing a capture antibody (specific for the antigen) onto a solid support followed by addition of an amount of antigen. The bound antigen is then detected by a second antibody (i.e., detection antibody) which recognizes a region on the antigen that is different from that of the capture antibody. The captured antigen is detected by the detection antibody which can be covalently linked to an enzyme, or can itself be detected by addition of a secondary antibody which is linked to an enzyme.

Kits:

Another aspect of the invention is to provide a kit that may be used to detect anti-*Felis catus* gammaherpesvirus 1 (FcaGHV1) antibodies in domestic cats and other felines. The kit according to the present invention includes a set of antigens (e.g. polypeptides encoded by ORF52 and ORF38) that are specifically bound by anti-FcaGHV1 antibodies. In one embodiment, the kit contains reagents (e.g., precipitating chemicals such as acetone or TCA) for treating the urine sample so as to enable DEK protein to be detected from the sample. In one embodiment, the kit contains ELISA plates necessary to perform indirect ELISA to detect anti-FcaGHV1 antibodies.

Kits provided herein include instructions, such as a package insert having instructions thereon, for using the reagents to prepare and preparing samples. Such instructions may be for using the reagents to prepare the blood sample to specifically allow detection of anti-FcaGHV1 antibodies from the blood sample of the feline. In another embodiment, the instructions are directed to the use of recombinant antigens (e.g. polypeptides encoded by ORF52 and ORF38) that are recognized and bind to anti-FcaGHV1 antibodies in Western blot analysis or ELISA.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.: as well as Guthrie et al., Guide to Yeast Genetics and Molecular Biology, Methods in Enzymology, Vol. 194, Academic. Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of detecting antibodies to *Felis catus* gammaherpesvirus 1 (FcaGHV1) in a test sample obtained from a feline comprising the steps of:
   obtaining a test sample, wherein the test sample is blood, serum or plasma sample; and
   performing an immunoassay comprising:
      contacting the test sample with full-length recombinant FcaGHV1 ORF38 and ORF52 polypeptides; and
      detecting binding between antibodies to FcaGHV1 in the test sample and at least one of the full-length recombinant FcaGHV1 polypeptides, whereby the presence of binding between antibodies to FcaGHV1 in the sample and one of the recombinant FcaGHV1 polypeptides is indicative of antibodies to FcaGHV1 in the test sample.

2. The method according to claim 1, wherein the test sample obtained from a feline is a test sample from a domestic cat.

3. The method according to claim 1 wherein the immunoassay is an IFA, a western blot assay or an ELISA.

4. The method according to claim 1 wherein the immunoassay is an indirect ELISA.

5. The method of detecting antibodies to FcaGHV1 in a test sample according to claim 1, wherein the test sample is blood, further comprising the step of performing qPCR on the blood sample to screen for FcaGHV1 nucleic acid.

6. The method of detecting antibodies to FcaGHV1 in a test sample according to claim 1 further comprising:
   contacting the test sample with additional full-length recombinant FcaGHV1 polypeptides selected from the group consisting of ORF17.5, ORF65, LANA, and combinations thereof; and
   detecting binding between antibodies to FcaGHV1 in the test sample and at least one of the additional recombinant FcaGHV1 polypeptides.

7. A method of detecting antibodies to *Felts catus* gammaherpesvirus 1 (FcaGHV1) in a test sample obtained from a feline comprising the steps of:
   obtaining the test sample, wherein the test sample is a blood, serum or plasma sample;
   performing an immunoassay comprising:
      contacting the test sample with full-length recombinant FcaGHV1 ORF38 and ORF52 polypeptides; and
         detecting binding between antibodies to FcaGHV1 in the test sample and at least one of the full-length recombinant FcaGHV1
      polypeptides, whereby the presence of binding between antibodies to FcaGHV1 in the sample and one of the recombinant FcaGHV1 polypeptides is indicative of antibodies to FcaGHV1 in the test sample; and
   performing qPCR on the sample, wherein the sample is blood, to screen for FcaGHV1 nucleic acid.

* * * * *

SEQUENCE LISTING

```
<160> NUMBER OF SEQ ID NOS: 16

<210> SEQ ID NO 1
<211> LENGTH: 29
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 1
agacgctgat caatggccac taatgccag                                         29
```

<210> SEQ ID NO 2
<211> LENGTH: 41
<212> TYPE: DNA
<213> ORGANISM: Artificial Sequence
<220> FEATURE:
<223> OTHER INFORMATION: Primers used to amplify FcaGHv1 genes and pKH3 vector.

<400> SEQUENCE: 2
cctgaattcc tattagtttt ttagaagttc ttcacaaaat a               41

<210> SEQ ID NO 3
<211> LENGTH: 31
<212> TYPE: DNA
<213> ORGANISM: Artificial Sequence
<220> FEATURE:
<223> OTHER INFORMATION: Primers used to amplify FcaGHv1 genes and pKH3 vector.

<400> SEQUENCE: 3
cgcggatcca tgggtatcat ctgctctatt t                          31

<210> SEQ ID NO 4
<211> LENGTH: 43
<212> TYPE: DNA
<213> ORGANISM: Artificial Sequence
<220> FEATURE:
<223> OTHER INFORMATION: Primers used to amplify FcaGHv1 genes and pKH3 vector.

<400> SEQUENCE: 4
ccggaattcc tatcagatac taaatacaac tttctttttt atc             43

<210> SEQ ID NO 5
<211> LENGTH: 32
<212> TYPE: DNA
<213> ORGANISM: Artificial Sequence
<220> FEATURE:
<223> OTHER INFORMATION: Primers used to amplify FcaGHv1 genes and pKH3 vector.

<400> SEQUENCE: 5
cgcggatcca tggcttctaa aaaaggaaca cc                         32

<210> SEQ ID NO 6
<211> LENGTH: 35
<212> TYPE: DNA
<213> ORGANISM: Artificial Sequence
<220> FEATURE:
<223> OTHER INFORMATION: Primers used to amplify FcaGHv1 genes and pKH3 vector.

<400> SEQUENCE: 6
cctgaattcc tattaggttg gttgtttgga tctac                      35

<210> SEQ ID NO 7
<211> LENGTH: 31
<212> TYPE: DNA
<213> ORGANISM: Artificial Sequence
<220> FEATURE:
<223> OTHER INFORMATION: Primers used to amplify FcaGHv1 genes and pKH3 vector.

<400> SEQUENCE: 7
cgcggatcca tgagtaggga acagttaaga g                          31

<210> SEQ ID NO 8

```
<211> LENGTH: 38
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 8
ccggaattcc tattattttt ttttgcttcc actagttg                              38

<210> SEQ ID NO 9
<211> LENGTH: 36
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 9
cgcggatcca tgcaagttga taaaaaaatc atagtc                                36

<210> SEQ ID NO 10
<211> LENGTH: 31
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 10
ccggaattcc tactagatgg acaaccagcc t                                     31

<210> SEQ ID NO 11
<211> LENGTH: 35
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 11
cgcggatcca tggaagctaa aattactact cacta                                 35

<210> SEQ ID NO 12
<211> LENGTH: 38
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 12
ccggaattcc tattatgttg taatcttgga atgttttg                              38

<210> SEQ ID NO 13
<211> LENGTH: 30
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 13
cgcggatcca tggactctgt aatccgaacc                                       30

<210> SEQ ID NO 14
<211> LENGTH: 39
```

```
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 14
cctgaattcc tattatgaaa agatttgtac tctaggctt                              39

<210> SEQ ID NO 15
<211> LENGTH: 19
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 15
caactgcacc tcggttcta                                                    19

<210> SEQ ID NO 16
<211> LENGTH: 25
<212> TYPE: DNA
<213> ORGANISM: Artificial Sequence
<220> FEATURE:
<223> OTHER INFORMATION: Primers used to amplify FcaGHV1 genes and pKH3
      vector.

<400> SEQUENCE: 16
ccattataag ctgcaataaa caagt                                             25
```